(12) United States Patent
Giudiceandrea et al.

(10) Patent No.: US 12,148,142 B2
(45) Date of Patent: Nov. 19, 2024

(54) INDUSTRIAL TOMOGRAPHY APPARATUS AND METHOD FOR CHECKING THE INTEGRITY OF INDUSTRIAL PRODUCTS

(71) Applicant: BIOMETIC S.R.L., Bressanone (IT)

(72) Inventors: Arianna Giudiceandrea, Bressanone (IT); Enrico Ursella, Mestre (IT); Giancarlo Zane, Mestre (IT)

(73) Assignee: BIOMETIC S.R.L., Bressanone (IT)

( * ) Notice: Subject to any disclaimer, the term of this patent is extended or adjusted under 35 U.S.C. 154(b) by 442 days.

(21) Appl. No.: 17/391,451

(22) Filed: Aug. 2, 2021

(65) Prior Publication Data
US 2022/0044381 A1 Feb. 10, 2022

(30) Foreign Application Priority Data
Aug. 7, 2020 (IT) .................. 102020000019819

(51) Int. Cl.
*G06K 9/00* (2022.01)
*B65B 57/00* (2006.01)
(Continued)

(52) U.S. Cl.
CPC .............. *G06T 7/001* (2013.01); *B65B 57/00* (2013.01); *G06T 7/97* (2017.01); *G01N 33/0081* (2024.05);
(Continued)

(58) Field of Classification Search
CPC ........... G06T 2207/10072; G06T 15/08; G06T 17/00; G06T 2207/10081; G06T 7/001;
(Continued)

(56) References Cited

U.S. PATENT DOCUMENTS 9,816,949 B2 * 11/2017 Santini ...................... G06T 5/20
10,481,108 B2 5/2019 Ferro et al.
(Continued)

FOREIGN PATENT DOCUMENTS

EP 2405260 1/2012
WO 9718462 5/1997

OTHER PUBLICATIONS

Hindelang, F., Zurbach, R., & Roggo, Y. (2015). Micro computer tomography for medical device and pharmaceutical packaging analysis. Journal of Pharmaceutical and Biomedical Analysis, 108, 38-48. (Year: 2015).*
(Continued)

*Primary Examiner* — Gregory A Morse
*Assistant Examiner* — Kevin M Coomber
(74) *Attorney, Agent, or Firm* — Pearne & Gordon LLP; Michelle E. Tochtrop

(57) ABSTRACT

An industrial tomography apparatus comprising a tomography scan device configured to perform tomography scans of the products placed in the scanning zone and an electronic processing unit programmed to generate a virtual three-dimensional tomography model of a product scanned by the tomography scan device, and to perform a procedure for inspecting industrial products of known type, each comprising a packet or a container. During the inspection procedure the electronic processing unit inspects the virtual three-dimensional tomography model to assess internal features of the product and/or the shape of the product at predetermined zones and determines whether or not those internal features and/or respectively that shape, correspond to a product with intact packet or container. The apparatus implements a corresponding method for checking the integrity of packets or containers of industrial products which have known features.

12 Claims, 4 Drawing Sheets

(51) Int. Cl.
*G06T 7/00* (2017.01)
*G01N 33/00* (2006.01)

(52) U.S. Cl.
CPC ............... *G06T 2207/10072* (2013.01); *G06T 2207/30128* (2013.01)

(58) Field of Classification Search
CPC ...................... G06T 7/97; G06T 7/0004; G06T 2207/30108; G06T 2207/30128; G01N 23/046; G01N 2021/1787; G01N 23/18; G01N 2033/0081; G01N 33/02; G01N 21/90; G01N 2021/845; B65B 57/00
See application file for complete search history.

(56) References Cited

U.S. PATENT DOCUMENTS

| | | |
|---|---|---|
| 2008/0260096 A1 | 10/2008 | Sommer et al. |
| 2011/0050880 A1 | 3/2011 | Bourg, Jr. et al. |
| 2016/0019688 A1* | 1/2016 | Li ........................ G06V 10/42 382/110 |
| 2016/0178539 A1* | 6/2016 | Santini ................... G01N 33/02 382/110 |
| 2016/0305895 A1 | 10/2016 | Ferro et al. |
| 2017/0352150 A1* | 12/2017 | Magana ..................... G06T 7/13 |
| 2017/0357857 A1 | 12/2017 | Perron |
| 2018/0113083 A1 | 4/2018 | Van Dael et al. |
| 2019/0137421 A1 | 5/2019 | Ferro et al. |
| 2019/0322570 A1 | 10/2019 | Gawronski |

OTHER PUBLICATIONS

Hindelang, Florine, et al., "Micro Computer Tomography for medical device and pharmaceutical packaging analysis", Journal of Pharmaceutical and Biomedical Analysis, Elsevier B.V., Amsterdam, NL, vol. 108, Feb. 9, 2015, pp. 38-48.

Chandiramani, Sumita, "Micro-CT Examination of Seal Integrity in Glass Vials", Retrieved from the Internet: URL: https://www.microphotonics.com/micro-ct-examination-of-seal-integrity-in-glass-vials/ [retrieved on Mar. 22, 2021], Oct. 29, 2019, 10 pages.

Cao, Wenchao, et al., "An Improved Segmentation Method for Multi-Material Beam Hardening Correction in Industrial X-Ray Computed Tomography", Measurement Science and Technology, 30.12 (2019): 125403, 23 pages.

* cited by examiner

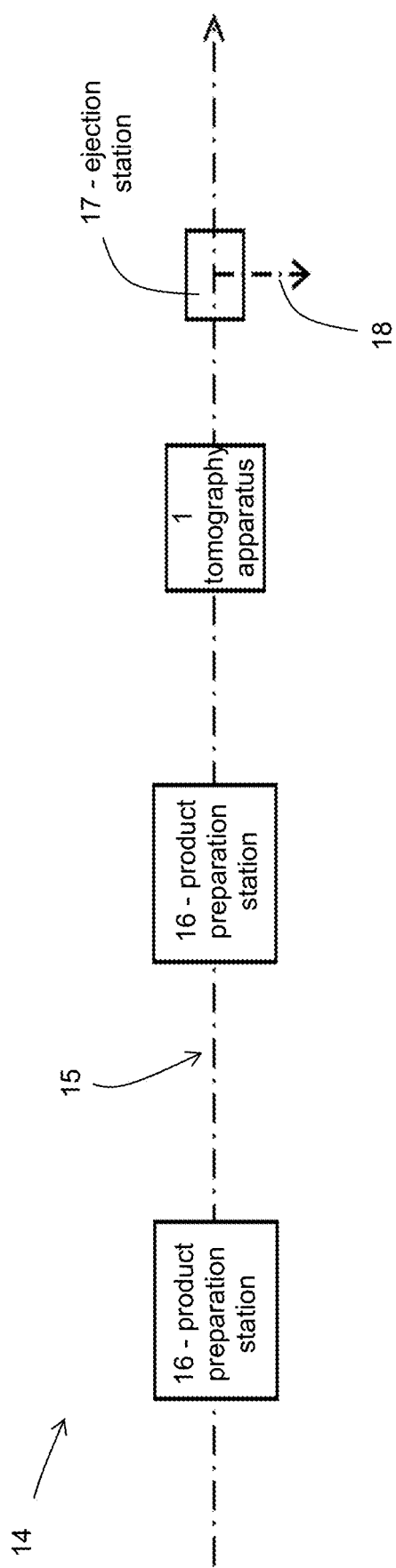
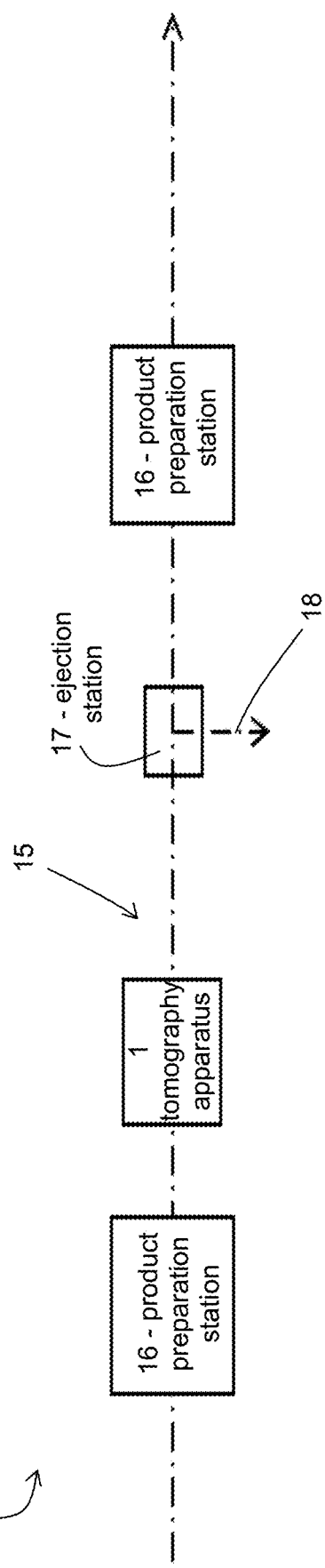
FIG. 9
FIG. 10

INDUSTRIAL TOMOGRAPHY APPARATUS AND METHOD FOR CHECKING THE INTEGRITY OF INDUSTRIAL PRODUCTS

This invention relates to an industrial tomography apparatus and a method for checking the integrity of industrial products. In particular, this invention relates to checking the integrity of the packet or of the container, of products which are vacuum-packed or packaged using modified pressure compared with atmospheric pressure. The term modified pressure refers to packaging using negative pressure or positive pressure compared with atmospheric pressure.

Some examples of application of this invention may be:

for vacuum packaging: ground coffee and coffee beans, dried fruit and nuts, salami and cold pork meat, dairy products, meats, etc.;

for packaging using negative pressure all foods packaged with containers (usually glass jars) closed with a lid having a safety pop-up button or with containers which, in a similar way to a lid having a safety pop-up button, at least locally change their shape; foods packaged in this way include tomato passata, items preserved in oil, pickles, cooked pulses, etc.

for packaging using positive pressure all foods packaged in MAP (Modified Atmosphere Packaging) such as meats, coffee pods, etc.

Although the widely preferred field of application is the food sector, this invention may be applied in any sector which has similar requirements linked to vacuum-packaging or packaging using modified pressure (for example in the pharmaceutical sector). Therefore, in the context of this invention, the definition industrial product is used to identify any product which is industrially made and/or packaged.

Moreover, the definition product also includes the packet or the container which are a part of it (for example the bag of multi-layer material in which ground coffee is packaged, or the jar and lid in which pickles are packaged) not just the contents.

In the context of this invention, when reference is made to the integrity of the product (or of the respective packet/container) the intention is to refer to the fact that the inside of the packet or of the container are in a vacuum or subject to modified pressure as expected.

In fact, for all of the products of the type described above, it is essential to guarantee correct vacuum-packaging or packaging using modified pressure, since correct packaging guarantees the quality and the correct preservation of the food product. In particular, it would be essential to guarantee that all of the products which come from the production and are shipped to customers are packaged correctly.

Although such a problem has been known and experienced for a very long time, until now companies have been able to face it by simply attempting to increasingly improve the production lines with the aim of minimising the occurrence of unwanted production/packaging errors. Furthermore, sampling checks have been proposed, to verify products a posteriori in a statistical way and to understand which interventions should be performed on the production plants if necessary (although in many cases the check by an operator may allow verifications of a failure of integrity, it is a check which in most cases is not feasible due to the excessively high productivity of the plants).

In contrast, as far as the Applicant is aware, until now on the market there are no known methods or apparatuses for checking a posteriori in an effective and systematic way the entire production of industrial products, with the aim of identifying any products whose packet or whose container are non-intact and in which the vacuum or negative pressure expected is not present.

That also makes it impossible for the company to immediately detect any problems with the packaging plant which result in the incorrect packaging of whole production batches.

In this context, the technical purpose which forms the basis of this invention is to overcome the above-mentioned disadvantages.

In particular, the technical purpose of this invention is to make an apparatus and provide a method for checking the integrity of industrial products.

Furthermore it is the technical purpose of this invention to make an apparatus and provide a method for checking the integrity of industrial products, which allow the verification to be performed in a systematic way on the whole production.

Furthermore it is the technical purpose of this invention to make an apparatus and provide a method for checking the integrity of industrial products, which allow prompt checks to be performed and prompt detection of any faults in the plants.

The technical purpose specified and the aims indicated are substantially achieved by an industrial tomography apparatus and a method for checking the integrity of industrial products, as described in the appended claims.

Further features and the advantages of this invention are more apparent in the detailed description, with reference to the accompanying drawings which illustrate several preferred, non-limiting embodiments, in which:

FIGS. 9 and 10 show two layouts of industrial plants which comprise a tomography apparatus according to this invention.

Figure 1:
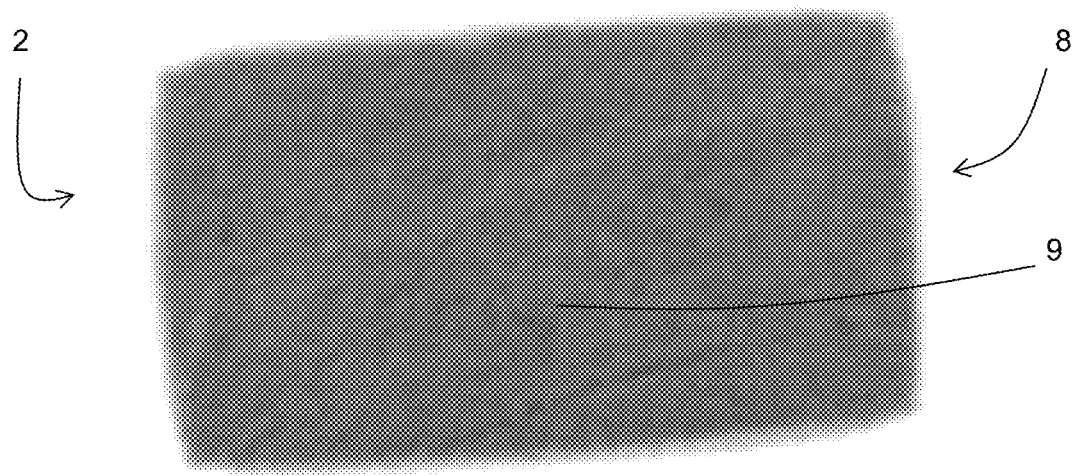
FIGS. 1 and 2 show two front views of virtual three-dimensional tomography models of packs of ground coffee with non-intact packet.

The following is a description initially of an industrial tomography apparatus made according to this invention and then of the method according to this invention. In any case, since the apparatus is capable of implementing the method according to this invention, what will be described relative to the tomography apparatus shall be understood to also apply for the method, and vice versa, if technically compatible. In fact, it shall be understood that particular embodiments of the apparatus will be capable of implementing only specific embodiments of the method, and that particular embodiments of the method can be implemented exclusively by specific embodiments of the apparatus.

The industrial tomography apparatus 1 according to this invention is a tomography apparatus specifically intended for analysing one or more products 2 of known type, and in particular products 2 of known type which comprise a packet 10 or a container 11 and which are vacuum-packed or packaged using modified pressure. Such products 2 of known type, hereinafter referred to simply as "products", have known features, as a whole (for example: overall size, list of primary parts of which they are composed) and as regards the individual parts of which they are composed, and as regards their packet 10 or container 11.

In any case, it should be noticed that, in the context of this invention, when reference is made to known features of the products 2 the intention is to also refer to the theoretical features which the products 2 should have, that is to say, to the features of products 2 which reflect the specifications for production and/or packaging in a vacuum or, respectively packaging using modified pressure. In contrast, as will be seen below, what this invention allows is a true verification, on the finished product 2, of whether or not said specifications are met.

Figure 8:
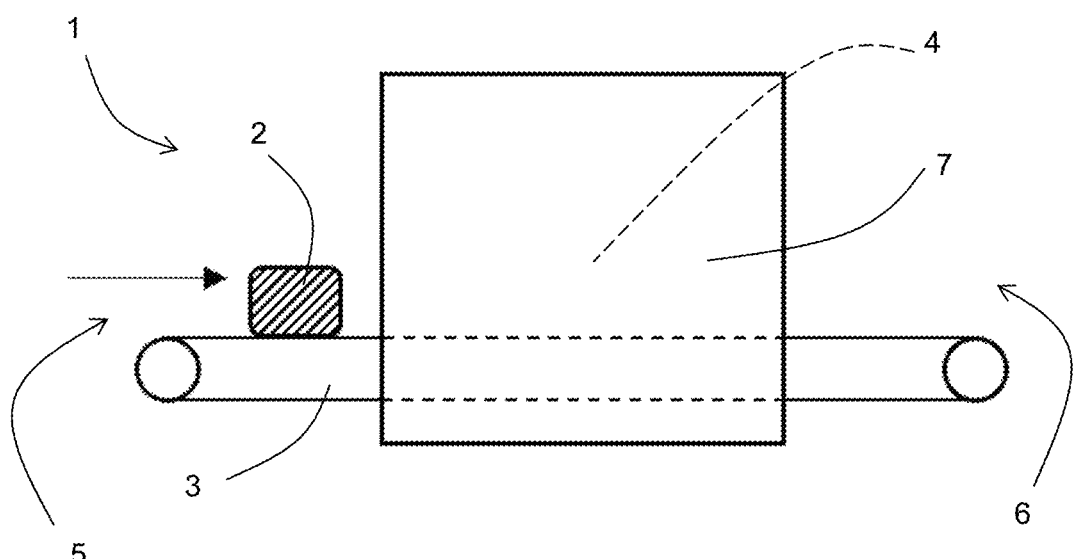
FIG. 8 shows an in line version of the tomography apparatus according to this invention.

The apparatus comprises first a conveying device 3 which is configured to feed the products 2 to be inspected to a scanning zone 4, and then to remove the products 2 from the scanning zone 4. Advantageously, the conveying device 3 moves in one direction from an infeed zone 5 to an outfeed zone 6 (FIG. 8), through the scanning zone 4.

At the scanning zone 4 there is a tomography scan device 7, which is configured to perform tomography scans of what is located in the scanning zone 4 and, in particular, of the industrial products 2 of interest. In the known way, the tomography scan device 7 comprises an x-ray emitter and an x-ray detector (which are not illustrated) placed on opposite sides of the scanning zone 4, and a movement system (also not illustrated) for making the product 2 rotate relative to the emitter and receiver (preferred solution) or vice versa. Since these are technical solutions known to experts in the sector, they will not be described in detail herein.

The tomography apparatus 1 also comprises an electronic processing unit (not illustrated) which is operatively connected to the tomography scan device 7, for receiving from it digital data about the tomography scans performed by the tomography scan device 7, from different relative angles relative to the object.

The electronic processing unit is programmed, in the known way, to use the digital data to generate a virtual three-dimensional tomography model (in electronic format) of each product 2 scanned by the tomography scan device 7. In an equally known way, the virtual three-dimensional tomography model 8 is constituted of a plurality of voxels (primary volumes), each of which is assumed to have its own constant density. Therefore, in the known way, associated with each voxel there is a value which is representative of the density of the voxel (CT Number). It should be noticed that the CT Number does not express the density in $g/dm^3$, but the value in $g/dm^3$ may generally be calculated provided that one knows the material of which the voxel is composed (for example chocolate, iron, etc.); in fact, for that purpose there are specific known beam-hardening correction algorithms (for example, see what is described in Cao, Wenchao, et al. "An improved segmentation method for multi-material beam hardening correction in industrial x-ray computed tomography." Measurement Science and Technology 30.12 (2019): 125403). In this way it is potentially possible to use the system even for calculating the weight/ the mass of the individual voxels if their volume is known.

It will be possible to select the dimensions of the voxels based on the dimensions of the product 2 to be inspected; in general they will be small enough to allow the obtainment of a sufficiently detailed and precise reconstruction. The virtual three-dimensional tomography model 8 is then advantageously saved in an electronic memory associated with the electronic processing unit.

According to a first innovative aspect of this invention, the electronic processing unit is also programmed to perform a procedure for inspecting the products 2 of known type to which the industrial tomography apparatus 1 is dedicated.

In particular, during the inspection procedure performed by it, the electronic processing unit inspects the virtual three-dimensional tomography model 8 of each product 2, to assess internal features of the product 2 and/or the shape of the product 2 at predetermined zones, with the aim of determining whether or not those internal features and/or respectively that shape, correspond to a product with intact packet 10 or container 11.

In some embodiments, during the inspection procedure the electronic processing unit assesses at least one of the following internal features of the product: the average density of the product, and the amount of empty space relative to the total volume of the product delimited by the packet 10 or by the container 11. This approach is advantageous in the case of products with non-rigid packets, which when they have a vacuum or a negative pressure inside them occupy a smaller volume than when they are at atmospheric pressure (e.g.: vacuum-packed bags of ground coffee, bags of dried fruit and nuts, packets of salami and cold pork meat or meats), and which when they are in positive pressure occupy a greater volume than when they are at atmospheric pressure. It should be noticed that since this invention is advantageously usable in the context of a production plant, the atmospheric pressure may always be known both at the moment of packaging the product, and at the moment of the tomography check.

In some embodiments, during the inspection procedure the electronic processing unit in contrast assesses the shape of the product, in particular verifying at least one of the following features: the trend of a profile of intersection between the virtual three-dimensional tomography model 8 and a predetermined plane, the trend of a profile of intersection between the virtual three-dimensional tomography model 8 and a predetermined surface which is not flat, the planarity of a predetermined portion of an external surface of the virtual three-dimensional tomography model 8, the curvature of the predetermined portion of the external surface of the virtual three-dimensional tomography model 8.

In some embodiments, the inspection procedure which the electronic processing unit is programmed to perform for each product 2 of known type, comprises a sequence of operating steps programmed in the electronic processing unit. The most general solution in particular comprises a segmentation step, an assessment step, a comparison step and a classification step.

When it performs the segmentation step, the electronic processing unit identifies inside the virtual three-dimensional tomography model 8 an internal volume 9.

Even the information about the internal volume 9 identified may then be saved. In some embodiments, during the segmentation step the electronic processing unit identifies as the internal volume 9 the volume contained by the packet 10 or respectively by the container 11, including the volume of the packet 10 or respectively of the container 11.

In contrast, in other embodiments, during the segmentation step the electronic processing unit identifies as the internal volume 9 the volume contained by the packet 10 or respectively by the container 11, not including the volume of the packet 10 or respectively of the container 11.

Moreover, in some embodiments, during the segmentation step the electronic unit may also identify the total volume of empty space in the internal volume (9), by simply selecting all of the voxels which have a density close to that of the space or of the air, for example in a predetermined range of densities between 0.00 g/m$^3$ and 50 kg/m$^3$ (notice that the upper limit is advantageously relatively high, so as to minimise the possible influence of noise).

During the assessment step, the electronic processing unit then assesses one or more predetermined properties of the internal volume 9 identified during the segmentation step. Regarding the predetermined properties of the internal volume 9 identified in the virtual three-dimensional tomography model 8, the same considerations set out above also apply for the internal features and the shape of the virtual three-dimensional tomography model 8 since the internal volume 9 constitutes the significant part of the virtual three-dimensional tomography model 8.

Then, the electronic processing unit is programmed to perform the comparison step, during which it compares the one or more predetermined properties assessed during the assessment step, with corresponding reference values saved in an electronic memory associated with the electronic processing unit. The reference values are simply the quantification of reference predetermined properties which correspond to a product 2 which reflects the production specifications. The aim of the comparison step is to verify if there is a match between the predetermined properties assessed during the assessment step and the reference values saved.

As regards possible practical implementations of the assessment and comparison steps, several examples are listed below.

In some cases, during the assessment step, the electronic processing unit assesses the average density of the product by calculating the average density of the internal volume 9, and during the comparison step compares it with a range of average density values which is considered acceptable. It should be noticed for example that usually a vacuum-packed product 2, with intact non-rigid packet 10, has an average density greater than a product 2 with similar packet 10 which is non-intact, whilst in the case of a product 2, packaged in MAP with packet 10 which is non-intact, the average density may be greater than a product 2 with similar packet 10 which is non-intact.

In some embodiments, during the assessment step the electronic processing unit calculates the volume of the internal volume 9 and the total volume of empty space present in the internal volume 9 and then assesses the amount of empty space present in the product 2, relative to the total volume of the product 2 delimited by the packet 10 or respectively by the container 11, comparing the total volume of empty space calculated to the volume of the internal volume 9 calculated.

In some applications, during the assessment step, the electronic processing unit in contrast assesses the shape of the product verifying at least one of the following features: the trend of a profile of intersection between the internal volume 9 and a predetermined plane, the trend of a profile of intersection between the internal volume 9 and a predetermined surface which is not flat, the planarity of a predetermined portion of an external surface of the internal volume 9, the curvature of the predetermined portion of the external surface of the internal volume 9.

Furthermore, whilst in some embodiments the assessment and comparison steps are performed as two successive steps, in which the electronic processing unit proceeds with quantitative assessments, in other embodiments the assessment and comparison steps may be performed simultaneously and in such a way that they are not separate. In the latter case in particular the electronic processing unit comprises a neural network, or respectively a deep neural network, programmed to simultaneously perform the assessment and comparison steps, processing the virtual three-dimensional tomography model 8 identified during the segmentation step.

Since, as already indicated, the tomography apparatus 1 disclosed is specifically intended for inspecting products 2 of known type, the neural network, or respectively the deep neural network, is a network which must be trained in advance by supplying it with specific training input and output data. The input data will comprise a first and a second plurality of internal volumes identified by using the segmentation step to process virtual three-dimensional tomography models 8. The virtual three-dimensional tomography models 8 of the first plurality are models of products 2 of the same type with intact packet 10 or container 11. In contrast, the virtual three-dimensional tomography models of the second plurality are models of products 2 of the same type with non-intact packet 10 or container 11.

Since the products 2 are of known type it is easy to have available the models of the first group, and, on the other hand, it is relatively simple to specially create "faulty" products 2 in order to obtain the models of the second group. It will be possible for the training output data to simply consist of a definition of product 2 with intact packet 10 or container 11, or of product 2 with non-intact packet 10 or container 11.

Finally, during the classification step the electronic processing unit supplies an indication about the result of the comparison step, and in particular an indication of intact packet 10 or container 11 if the comparison step identified a match for the predetermined properties assessed, and an indication of non-intact packet 10 or container 11 if the comparison step identified a failure to match for the predetermined properties assessed.

Depending on the embodiments, the indication may be supplied in many different ways. In particular it may be supplied to an operator by means of a screen, or it may be transmitted to other apparatuses of the plant in which the apparatus is mounted. Moreover, it may be saved in combination with the data about that product 2.

Figure 2:
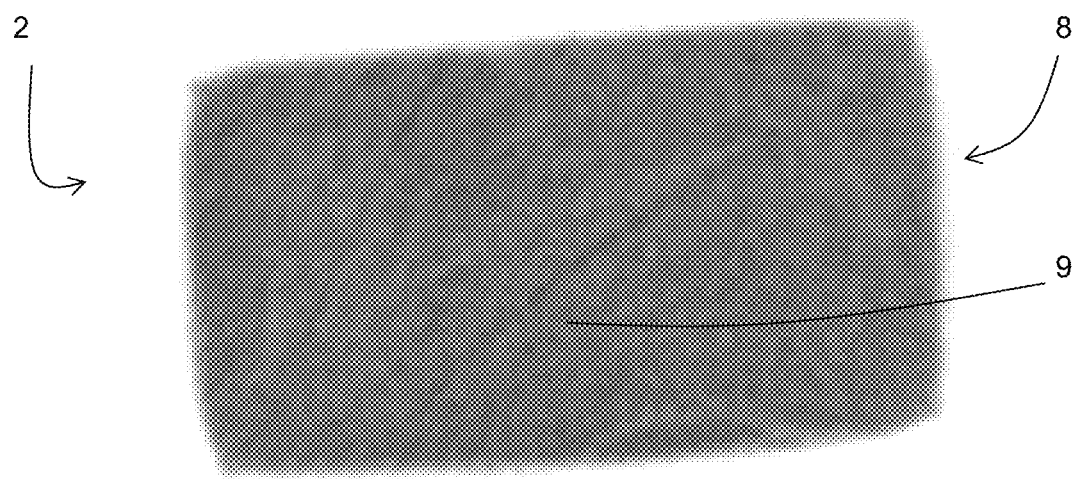
Figure 3:
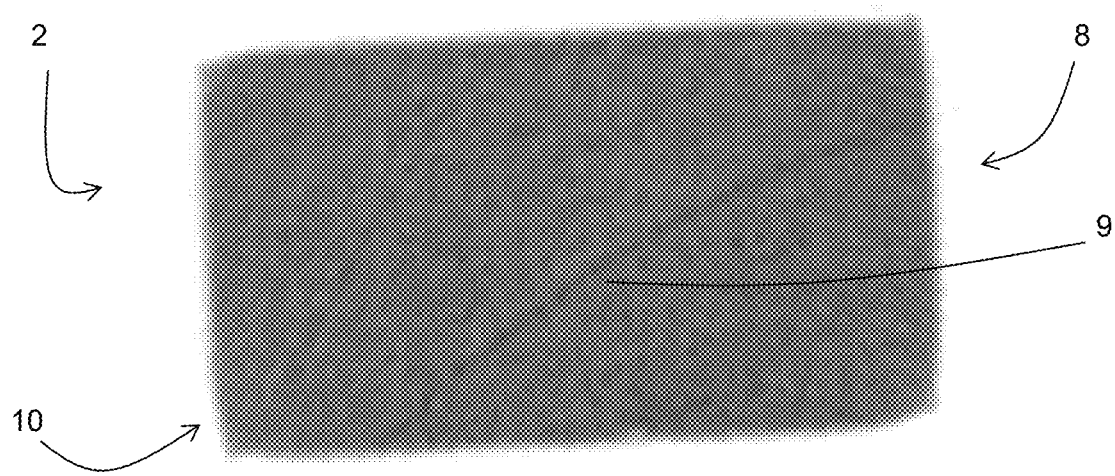
FIG. 3 shows a front view of a virtual three-dimensional tomography model of a pack of ground coffee with packet which is intact.
Figure 4:
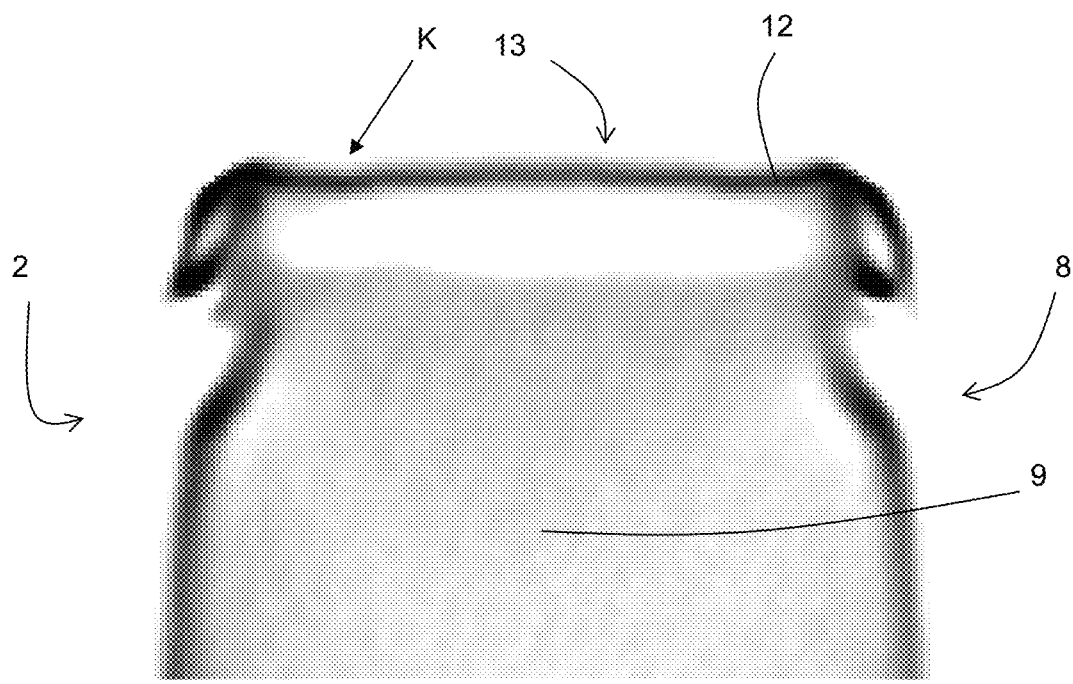
FIG. 4 shows a part of an axial section of a virtual three-dimensional tomography model of a jar of jam with a non-intact container (lid not deformed)
Figure 5:
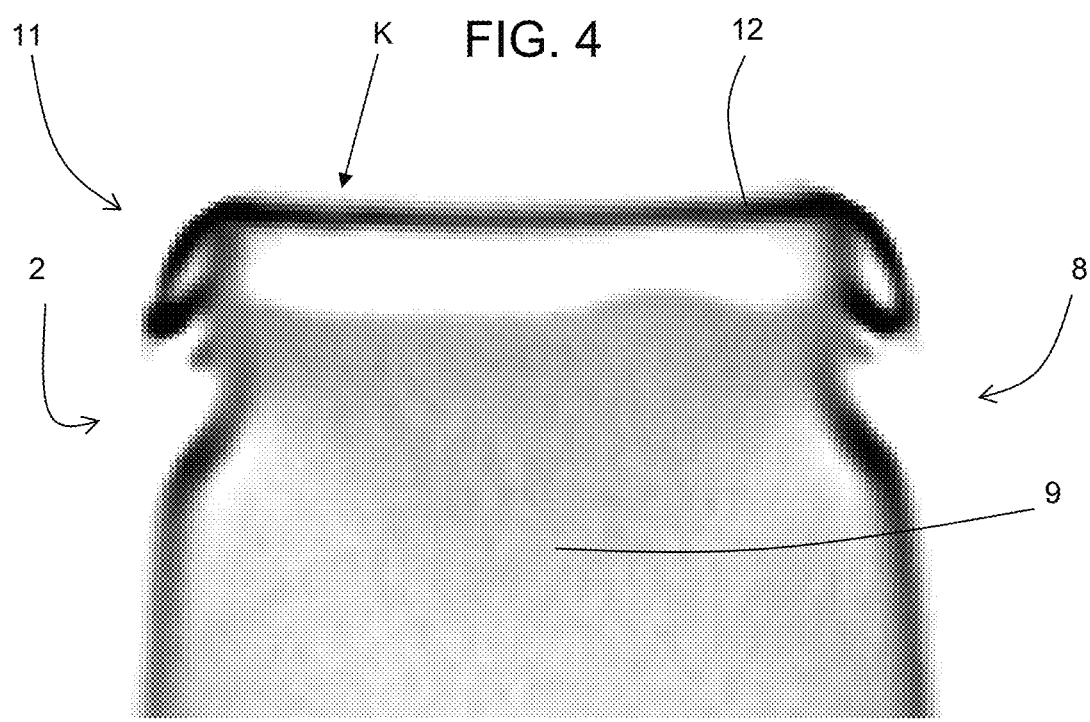
FIG. 5 shows a part of an axial section of a virtual three-dimensional tomography model of a jar of jam with a container which is intact (lid deformed)
Figure 6:
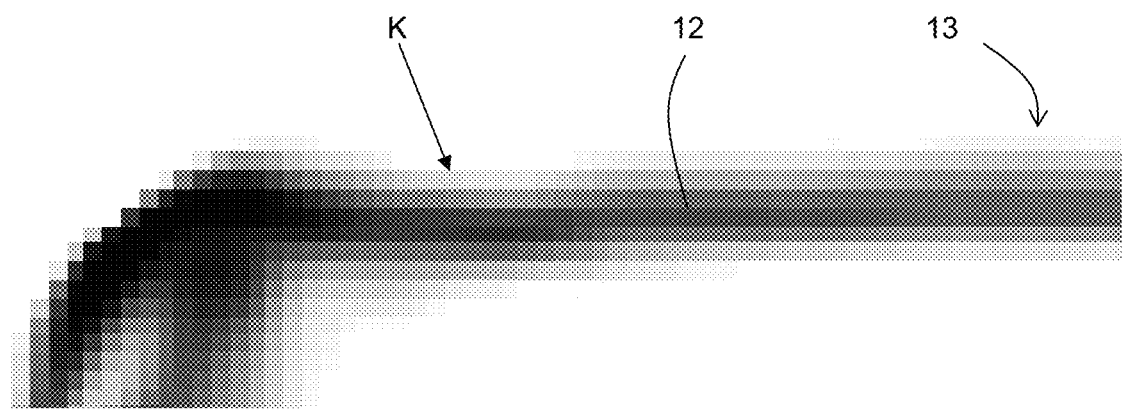
FIGS. 6 and 7 show two enlarged views, respectively of FIG. 4 and FIG. 5, of half of the lid of the container.
Figure 7:
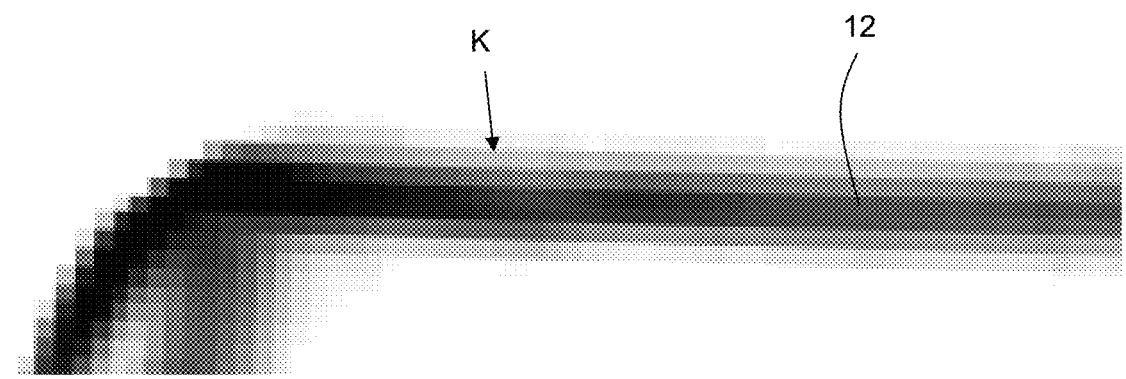

FIGS. 1 to 3 shows several examples of products 2 (bags of ground coffee) with a packet 10 which is intact (FIG. 3) or non-intact (FIGS. 1 and 2). It should be noticed how in the case an of intact packet 10 the volume of the product 2 is slightly smaller and the edges of the pack are more straight. In contrast, FIGS. 4 to 7 show two examples of products 2 (jars of jam) with a container 11 (jar) which is rigid except for the lid 12 which closes it. FIGS. 4 and 6 show the case of a non-intact container 11, since the lid 12 with safety pop-up button is not deformed and forms the characteristic bump at the centre, whilst FIGS. 5 and 7 show the case of an intact container 11, since the lid 12 with safety pop-up button is deformed and does not form the characteristic bump at the centre. In the former case, a horizontal plane (relative to the drawing) which is at a tangent to the lid 12 at the annular zone indicated by the letter K in the figures, intersects the central part of the lid 12 (of the container 11), whilst in the latter case it does not intersect it.

In other embodiments of this invention, in contrast the electronic processing unit comprises a neural network or a deep neural network which perform the entire inspection procedure (therefore, not just the assessment and comparison steps as in the case previously described).

The neural network, or respectively the deep neural network, is programmed to process the whole virtual three-dimensional tomography model 8 in order to establish whether or not the internal features and/or respectively the shape of the product 2, correspond to a product 2 with intact packet 10 or container 11. For that purpose, for each predetermined property to be inspected, the neural network, or respectively the deep neural network, was trained in advance by supplying them with specific training input and output data. The input data will comprise a first and a second plurality of virtual three-dimensional tomography models. The virtual three-dimensional tomography models of the first plurality are models of products 2 of the same type with intact packet 10 or container 11. In contrast, the virtual three-dimensional tomography models of the second plurality are models of products 2 of the same type with non-intact packet 10 or container 11.

In this case too, as in that previously described, obtaining the models of the first and second pluralities necessary as input data is simple.

As in the preceding case, it will be possible for the training output data to simply consist of a definition of product 2 with intact packet 10 or container 11, or of product 2 with non-intact packet 10 or container 11.

The context of this invention covers both the tomography apparatus 1 itself, and a plant 14 for the industrial production of products 2, which includes it. In general the plant 14 comprises a production line 15, along which one or more product 2 preparation stations 16 are mounted one after another. In the context of this invention preparation station 16 means any station which performs any processing on the product 2, whether it is a station for adding primary parts, for assembly, processing, packaging, etc.

An industrial tomography apparatus 1 according to what is described above is mounted along the production line 15 downstream of at least one preparation station 16 for the product 2, advantageously downstream of one or more preparation stations 16 in which operations are performed which may have an effect on the predetermined properties to be inspected In some embodiments, at the end of the inspection procedure the electronic processing unit classifies the product 2 as conforming and with intact packet 10 or container 11, or as non-conforming and with non-intact packet 10 or container 11, based on the predetermined properties assessed.

In some embodiments the electronic processing unit, at the end of the inspection procedure, classifies a product 2 as non-conforming when the comparison step has identified one or more failures to match.

In some embodiments the electronic processing unit, at the end of the inspection procedure, classifies a product 2 as non-conforming when the comparison step has identified, not just a failure to match, but also a difference, between the predetermined properties assessed and the corresponding reference values, which is above a maximum tolerance value. Moreover, in some embodiments, downstream of the industrial tomography apparatus 1, the plant 14 comprises an ejection station 17 configured to expel non-conforming products 2 from the production line 15 and to send them along a rejection or recovery path 18. Therefore, the electronic processing unit is connected (directly or indirectly) to the ejection station 17 for communicating to the ejection station 17 which products 2 have been classified as non-conforming. The plant 14 will also be equipped with a tracking system for the position of each individual product 2 along the production line 15 in such a way as to be able to precisely establish when each product 2 inspected by the industrial tomography apparatus 1, arrives in the ejection station 17. The industrial tomography apparatus 1 and the ejection station 17 may be positioned either at the end of the production line 15 (FIG. 15) or at a position in the middle of it (FIG. 16).

In some embodiments, alternatively or in addition to classification of the product 2 as conforming or non-conforming, the plant 14 comprises a checking system connected to the electronic processing unit for receiving from it information about the predetermined properties assessed.

Moving on to the method for checking the integrity of packets or containers of industrial products 2 which comprise a plurality of primary parts in accordance with this invention, many aspects of it may be inferred from the above description of the apparatus.

It comprises first a tomography scan step, wherein, by means of a tomography apparatus 1 inserted in a production line 15, a computed tomography scan of the product 2 including the packet 10 or container 11 is performed, and a virtual three-dimensional tomography model 8 of it is obtained, constituted of a plurality of voxels, each of which is assumed to have its own constant density (see what is indicated above).

This is followed by performing a step of computerised analysis of the virtual three-dimensional tomography model 8, wherein the internal features of the product 2 and/or the shape of the product 2 at predetermined zones are assessed, in order to determine whether or not those internal features and/or respectively that shape, correspond to a product with intact packet 10 or container 11.

Obviously, the internal features and the verifications of the shape may be the same as those previously indicated.

In some embodiments, the computerised analysis step comprises a segmentation step, an assessment step, a comparison step and a classification step whose operations correspond to those described above with reference to programming of the electronic processing unit.

In other embodiments, the computerised analysis step is wholly or partly implemented by means of neural networks, or deep neural networks, similarly to what was described above with reference to the apparatus.

This invention brings important advantages.

In fact, thanks to this invention it has been possible to provide an apparatus and a method which allow systematic checking of the integrity of the packet or of the container of the whole production of industrial products of known type.

Second, this invention, applied in the context of a production plant, allows the earliest possible detection of any packaging faults and allows a reduction in the incidence of defective production batches.

A further advantage of this invention consists of having provided an apparatus and a method which allow checking of the integrity of the packet or of the container of industrial product of known type even when the packet or the container are in turn contained in a further packing which prevents any visual inspection.

The invention described above may be modified and adapted in several ways without thereby departing from the scope of the inventive concept.

All details may be substituted with other technically equivalent elements and the materials used, as well as the shapes and dimensions of the various components, may vary according to requirements.

The invention claimed is:

1. An industrial tomography apparatus (1) comprising:
a conveying device (3), configured to feed to a scanning zone (4), and respectively remove from the scanning zone (4), industrial products (2) to be inspected;
a tomography scan device (7) configured to perform tomography scans of a product (2) placed in the scanning zone (4); and
an electronic processing unit operatively connected to the tomography scan device (7) for receiving from it digital data about the tomography scans performed by the tomography scan device (7), and programmed to generate, using that digital data, a virtual three-dimensional tomography model (8) of the product (2) scanned by the tomography scan device (7), the virtual three-dimensional tomography model (8) being constituted of a plurality of voxels;
and wherein the electronic processing unit is also programmed to perform a procedure for inspecting industrial products (2) of known type, each comprising a packet (10) or a container (11) and being vacuum-packed or packaged using modified pressure compared with atmospheric pressure, and wherein during the inspection procedure the electronic processing unit:
inspects the virtual three-dimensional tomography model (8) to assess internal features of the product (2) and/or the shape of the product (2) at predetermined zones; and
determines whether or not those internal features and/or respectively that shape, correspond to a product with intact packet (10) or container (11), wherein an inside of the packet or of the container is in a vacuum or subject to modified pressure;
wherein, during the inspection procedure the electronic processing unit:
assesses at least one of the following internal features of the product: the average density of the product, the amount of empty space relative to a total volume of the product delimited by the packet (10) or by the container (11); and/or
assesses the shape of the product by verifying at least one of the following features: the trend of a profile of intersection between the virtual three-dimensional tomography model (8) and a predetermined plane, the trend of a profile of intersection between the virtual three-dimensional tomography model (8) and a predetermined surface which is not flat, the planarity of a predetermined portion of an external surface of the virtual three-dimensional tomography model (8), the curvature of the predetermined portion of the external surface of the virtual three-dimensional tomography model (8);
wherein, the inspection procedure which the electronic processing unit is programmed to perform for assessing the internal features of the product (2), comprises the following operating steps:
a segmentation step, wherein in the virtual three-dimensional tomography model (8), the electronic processing unit identifies an internal volume (9) which is constituted of adjacent voxels;
an assessment step, wherein the electronic processing unit assesses one or more predetermined properties of the internal volume identified in the segmentation step;
a comparison step, wherein the electronic processing unit compares the one or more predetermined properties assessed during the assessment step with corresponding reference values saved in an electronic memory, to verify if there is a match; and
a classification step wherein the electronic processing unit supplies an indication of intact packet (10) or container (11), corresponding to the inside of the packet or of the container being in a vacuum or subject to modified pressure, if the comparison step identified a match for the predetermined properties assessed, and an indication of non-intact packet (10) or container (11), corresponding to the inside of the packet or of the container not being in a vacuum or subject to modified pressure, if the comparison step identified a failure to match for the predetermined properties assessed;
and additionally, wherein:
(i) the electronic processing unit calculates the internal volume (9) and the total volume of empty space in the internal volume (9) and, during the assessment step, the electronic processing unit assesses said one or more predetermined properties of the internal volume by comparing the calculated total volume of empty space to the calculated internal volume (9) to assess the amount of empty space relative to the total volume of the product delimited by the packet (10) or respectively by the container (11); or
(ii) during the assessment step, the electronic processing unit assesses the shape of the product verifying at least one of the following features: the trend of a profile of intersection between the internal volume (9) and a predetermined plane, the trend of a profile of intersection between the internal volume (9) and a predetermined surface which is not flat, the planarity of a predetermined portion of an external surface of the internal volume (9), the curvature of the predetermined portion of the external surface of the internal volume (9); or
during the assessment step, the electronic processing unit assesses the average density of the product by calculating the average density of the internal volume (9).

2. The industrial tomography apparatus (1) according to claim 1, wherein during the segmentation step the electronic processing unit identifies as the internal volume (9) the volume contained by the packet (10) or respectively by the container (11), including or not including the volume of the packet (10) or respectively of the container (11).

3. A plant (14) for the industrial production of products (2) comprising the packet (10) or the container (11), the products being vacuum-packed or packaged using modified pressure compared with atmospheric pressure, comprising a production line (15) along which one or more product (2) preparation stations (16) are mounted one after another, and at least one industrial tomography apparatus (1) according to claim 1 mounted along the production line (15) downstream of at least one preparation station (16) for the product (2).

4. The plant (14) according to claim 3, wherein, at the end of the inspection procedure, the electronic processing unit classifies a product (2) as conforming or non-conforming based respectively on whether or not it determines that packet (10) or container (11) integrity exists, wherein the plant (14), downstream of the industrial tomography apparatus (1) comprises an ejection station (17) configured to expel non-conforming products (2) from the production line (15), and wherein the electronic processing unit is connected to the ejection station (17) for communicating to the ejection station (17) which products (2) have been classified as non-conforming.

5. The plant (14) according to claim 4, wherein, at the end of the inspection procedure, the electronic processing unit classifies a product (2) as non-conforming and with non-intact packet (10) or container (11), when the comparison step has identified one or more failures to match and/or when the comparison step has identified, in the case of a failure to match, a difference between the predetermined properties assessed and the corresponding reference values which is above a maximum tolerance value.

6. A method for checking the integrity of packets or containers of industrial products (2) which have known features and are vacuum-packed or packaged using modified pressure compared with atmospheric pressure, the method comprising the following operating steps:
  a tomography scan step, wherein, by means of a tomography apparatus (1) inserted in a production line (15), a computed tomography scan of a product (2) including the packet (10) or container (11) is performed and a virtual three-dimensional tomography model (8) of it is obtained, constituted of a plurality of voxels; and
  a step of computerised analysis of the virtual three-dimensional tomography model (8), wherein the internal features of the product (2) and/or the shape of the product (2) at predetermined zones are assessed, in order to determine whether or not those internal features and/or respectively that shape, correspond to a product with intact packet (10) or container (11) wherein an inside of the packet or of the container is in a vacuum or subject to modified pressure;
  wherein, during the computerised analysis step:
  at least one of the following internal features of the product is assessed: the average density of the product, the amount of empty space relative to a total volume of the product delimited by the packet (10) or respectively by the container (11); and/or respectively
  the shape of the product is assessed by verifying at least one of the following features: the trend of a profile of intersection between the virtual three-dimensional tomography model (8) and a predetermined plane, the trend of a profile of intersection between the virtual three-dimensional tomography model (8) and a predetermined surface which is not flat, the planarity of a predetermined portion of an external surface of the virtual three-dimensional tomography model (8), the curvature of the predetermined portion of the external surface of the virtual three-dimensional tomography model (8);
  wherein, the computerised analysis step comprises:
  a segmentation step, wherein in the virtual three-dimensional tomography model (8), an internal volume (9) which is constituted of adjacent voxels is identified;
  an assessment step, wherein one or more predetermined properties of the internal volume (9) identified in the segmentation step are assessed;
  a comparison step, wherein the one or more predetermined properties assessed during the assessment step are compared with corresponding reference values saved in an electronic memory, to verify if there is a match; and
  a classification step wherein an indication of intact packet (10) or container (11), corresponding to the inside of the packet or of the container being in a vacuum or subject to modified pressure, is supplied if the comparison step identified a match for the predetermined properties assessed, and an indication of non-intact packet (10) or container (11), corresponding to the inside of the packet or of the container not being in a vacuum or subject to modified pressure, is supplied if the comparison step identified a failure to match for the predetermined properties assessed;
  and additionally, wherein:
  (i) the internal volume (9) and the total volume of empty space in the internal volume (9) are calculated and, during the assessment step, said one or more predetermined properties of the internal volume are assessed by comparing the calculated total volume of empty space to the calculated internal volume (9) to assess the amount of empty space relative to the total volume of the product delimited by the packet (10) or respectively by the container (11); or
  (ii) during the assessment step, the shape of the product is assessed verifying at least one of the following features: the trend of a profile of intersection between the internal volume (9) and a predetermined plane, the trend of a profile of intersection between the internal volume (9) and a predetermined surface which is not flat, the planarity of a predetermined portion of an external surface of the internal volume (9), the curvature of the predetermined portion of the external surface of the internal volume (9); or
  (iii) during the assessment step, the average density of the product is assessed by calculating the average density of the internal volume (9).

7. The method according to claim 6, wherein during the segmentation step what is identified as the internal volume (9) is the volume contained by the packet (10) or respectively by the container (11), including or not including the volume of the packet (10) or respectively of the container (11).

8. The method according to claim 6 wherein the products (2) are food products.

9. The method according to claim 7 wherein the products (2) are food products.

10. A plant (14) for the industrial production of products (2) comprising the packet (10) or the container (11) and vacuum-packed or packaged using modified pressure compared with atmospheric pressure, comprising a production line (15) along which one or more product (2) preparation stations (16) are mounted one after another, and at least one industrial tomography apparatus (1) according to claim 2 mounted along the production line (15) downstream of at least one preparation station (16) for the product (2).

11. The plant (14) according to claim 10, wherein, at the end of the inspection procedure, the electronic processing unit classifies a product (2) as conforming or non-conforming based respectively on whether or not it determines that packet (10) or container (11) integrity exists, wherein the plant (14), downstream of the industrial tomography apparatus (1) comprises an ejection station (17) configured to expel non-conforming products (2) from the production line (15), and wherein the electronic processing unit is connected to the ejection station (17) for communicating to the ejection station (17) which products (2) have been classified as non-conforming.

12. The plant (14) according to claim 11, wherein, at the end of the inspection procedure, the electronic processing unit classifies a product (2) as non-conforming and with non-intact packet (10) or container (11), when the comparison step has identified one or more failures to match and/or when the comparison step has identified, in the case of a failure to match, a difference between the predetermined properties assessed and the corresponding reference values which is above a maximum tolerance value.

* * * * *